United States Patent [19]

Ohra et al.

[11] Patent Number: 5,436,219

[45] Date of Patent: Jul. 25, 1995

[54] HERBICIDES WITH A CYCLIC HEXAPEPTIDE DEFERRIFERRICHROME AS AN ACTIVE INGREDIENT

[75] Inventors: Junko Ohra; Yasuko Tsujino, both of Yokohama, Japan

[73] Assignee: Japan Tobacco Inc., Tokyo, Japan

[21] Appl. No.: 142,379

[22] PCT Filed: Mar. 30, 1993

[86] PCT No.: PCT/JP93/00389

§ 371 Date: Nov. 29, 1993

§ 102(e) Date: Nov. 29, 1993

[87] PCT Pub. No.: WO93/19600

PCT Pub. Date: Oct. 14, 1993

[30] Foreign Application Priority Data

Mar. 31, 1992 [JP]  Japan .................. 4-104011

[51] Int. Cl.⁶ .................. A01N 43/713; A01N 63/02
[52] U.S. Cl. .................. 504/117; 504/220
[58] Field of Search .................. 504/220, 117

[56] References Cited

U.S. PATENT DOCUMENTS 3,365,287  1/1968  Zaehner et al. .................. 71/1

FOREIGN PATENT DOCUMENTS

| | | |
|---|---|---|
| 633630 | 12/1963 | Belgium . |
| 0197225 | 10/1986 | European Pat. Off. . |
| 1380523 | 10/1964 | France . |
| 224048 | 6/1985 | German Dem. Rep. . |
| 45-9833 | 4/1970 | Japan . |

OTHER PUBLICATIONS

H. P. Fiedler et al., European J. Appl. Microbiol. Biotecnol, Metabolic Products . . . , vol. 5, (1978), pp. 51–57.

Thomas F. Emery, Biochemistry, Initial Steps in the . . ., vol. 5, No. 11, (1966), pp. 3694–3701.

(List continued on next page.)

Primary Examiner—S. Mark Clardy
Attorney, Agent, or Firm—Birch, Stewart, Kolasch & Birch

[57] ABSTRACT

The present invention relates to herbicides comprising as an active ingredient a compound derived from a substance produced by a microorganism, which compound is represented by formula (I):

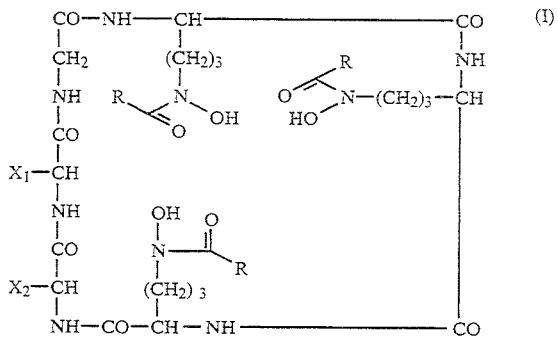

wherein $X_1$ and $X_2$ are the same or different and each represent a hydrogen atom, a methyl group or a hydroxymethyl group, R represents a methyl group, a hydroxymethyl group or the following formula:

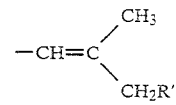

wherein R' represents a carboxyl group, a hydroxymethyl group or an acetoxymethyl group. The herbicide of the present invention exhibits a strong weed-killing effect on a wide range of plants such as broad-leaved weeds as well as weeds belonging to the family Gramineae.

15 Claims, No Drawings

OTHER PUBLICATIONS

Heidrun Anke et al., Biology of Metals, Production of siderophores . . . , vol. 4, (1991), pp. 176–180.

G. Demi et al., FEBS Letters, Tetraglycylferrichrome . . . , vol. 173, No. 1, (Jul. 1984), pp. 53–57.

A. Dell et al., Biomedical Mass Spectrometry, Field Desorption and . . . , vol. 9, No. 4, (1982), pp. 158–161.

C. L. Barnes et al., Acta. Cryst., Ferrichrome Conformations . . . , vol. 41, (1985), pp. 341–347.

Mahbubul A. F. Jalal et al., J. Org. Chem., Structure of . . . , vol. 50, No. 26, (1985), pp. 5642–5645.

M. A. F. Jalal et al., Biology of Metals, Structure of ferrichrome-type . . . , vol. 1, (1988), pp. 77–89.

M. Llinas et al., Biophysics of Structure and Mechanism, The Structure of . . . , vol. 2, (1976), pp. 105–117.

E. De. Hoffmann et al., Biological Mass Spectrometry, Fast Atom Bombardment Tandem . . . , vol. 20, (1991), pp. 142–152.

Allan Zalkin et al., Journal of the American Chemical Society, Ferrichrome-A Tetrahydrate . . . , vol. 88, No. 8, (Apr. 20, 1966), pp. 1810–1814.

CRC Handbook of Microbial Iron Chelates, pp. 16–19, 1975.

M. Llinas et al., J. Mol. Biol., C Nuclear Magnetic . . . , vol. 104, (1976), pp. 853–864.

Miguel Llinas et al., J. Mol. Biol., Solution Conformation . . . , vol. 52, (1970), pp. 399–414.

R. J. Kremer et al., Biological Abstracts, Characterization of . . . , vol. 90, Abst No. 47005 & Appl. Environ. Microbiol., vol. 56, No. 6, 1990, pp. 1649–1655.

Database WPI, Week 7746, Derwent Publications Ltd., London, GB; AN 77-81962Y [46] & JP-A-52 118 487 (Mitsubishi Chem Ind.) (Abstract) 1976.

C. L. Atkin et al., Chemical Abstracts, Leaf Infections. . . , vol. 77, No. 7, 1972, Abst. No. 43757 & Science, vol. 176, No. 4032, pp. 300–302.

Llinás et al. "Peptide Strain, . . . NMR Chemical Shifts in the Ferrichromes", *J. ACS* 99(11):3631–3637, May 25, 1977.

Reid et al. CA 105(15):132799 p. Abstract of *Biol. Fertil. Soils* 1(1):45–52, 1985.

Cline et al. CA 99(23):193766e, Abstract of *Soil Sci.* 136(3):145–157, 1983.

*Farm Chemicals Handbook '87*, "Micronutrient . . . " p. B 46, 1987.

HERBICIDES WITH A CYCLIC HEXAPEPTIDE DEFERRIFERRICHROME AS AN ACTIVE INGREDIENT

TECHNICAL FIELD

The present invention relates to a herbicide comprising as an active ingredient a cyclic hexapeptide derived from a substance produced by a microorganism.

BACKGROUND ART

Ever since 2,4-D was used as the means of chemically removing weeds, a numerous number of herbicides have been developed, and the time required for removal of weeds has thereby been drastically reduced. Because of anxiety about environmental pollution etc. raised in recent years, there is increasing demand for high-safety herbicides free from environmental pollution.

The present inventors have studied for the elucidation of toxins produced by plant-pathogenic microorganisms in order to obtain a novel substance having a weed-killing activity. By searching for a substance having a weed-killing activity among physiologically active substances produced by microorganisms, there is the possibility of finding a substance completely different from a synthetic compound with respect to the skeleton and nature of action. These naturally occurring substances are generally liable to enzyme degradation and thus least likely to remain in the environment. Out of such substances, bialaphos is a practically applied example developed by Meiji Seika Co., Ltd.

DISCLOSURE OF INVENTION

The object of the present invention is to provide herbicides comprising as an active ingredient a novel substance having a weed-killing activity derived from a substance produced by a microorganism.

The present inventors found a plant-toxic activity in an extract from a culture of plant-pathogenic microorganisms belonging to the genus Alternaria or Colletotrichum and that the activity itself is attributable to ferricrocin. As a result of further screening of compounds analogous to ferricrocin, the inventors isolated and identified ferrichrome, ferrichrome A and ferrichrome C from a culture extract of plant-pathogenic microorganisms belonging to the genus Ustilago.

Ferrichromes including the aforementioned ferricrocin, ferrichrome, ferrichrome A and ferrichrome C are represented by formula (II):

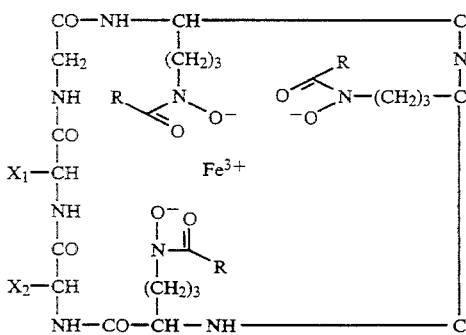

wherein $X_1$ and $X_2$ are the same or different and each represent a hydrogen atom, a methyl group or a hydroxymethyl group, R represents a methyl group, a hydroxymethyl group or the following formula:

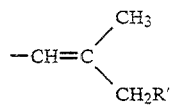

wherein R′ represents a carboxyl group, a hydroxymethyl group or an acetoxymethyl group. These ferrichromes are known cyclic hexapeptides having $Fe^{3+}$ in the molecule via a chelate bond (Winkelmann: "CRC Handbook of Microbial Iron Chelates" published by CRC Press, Inc., pp. 17–18 and p. 62), and there have already been some reports of these compounds which, as substances (siderophore) participating in the in vivo transfer of iron, are obtained from mold fungi such as the genera Aspergillus, Neurospora, etc. (See e.g. Eur. J. Appln. Microbiol. Biotechnol., 5(1), 51 (1978), Biochem., 5, 3694 (1966), Acta Cryst. C41, 341 (1985), and Biomedical Mass Spectrometry, 9(4), 158 (1982).)

The inventors found that the application of ferrichromes of formula (II) to the cut faces of cowpea blades leads to withering of the peripheries of the treated parts.

As a result of their further research, the inventors found that deferriferrichromes, i.e. compounds prepared by removal of intramolecular iron from ferrichromes of formula (II), have a strong weed-killing activity when applied not only to the cut faces of blades but also to intact blades. The deferriferrichromes are water-soluble, colorless substances obtainable by treating ferrichromes of formula (II) with a base, an acid, or a substance capable of forming an iron complex compound and their spectra as well as their properties as siderophore have already been known (see e.g. J. Mol. Biol., 52, 399 (1970), Japanese Patent Publication No. 9833/70, J. Mol. Biol. 104,853 (1976), J. Am. Chem. Soc., 88(8), 1810 (1966), Biological Mass Spectrometry, 20, 142 (1991), Biomedical Mass Spectrometry, 9(4), 158 (1982), Biophys. Struct. Mechanism, 2, 105 (1976), and Bio Metals, 1, 77 (1988)), but their weed-killing effect has never been known so far.

That is, the herbicide of the present invention comprises an active ingredient a compound represented by formula (I):

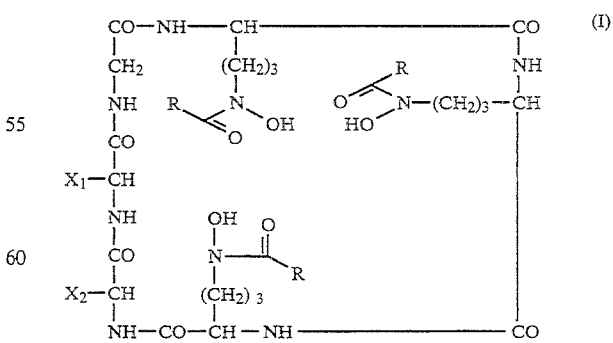

wherein $X_1$ and $X_2$ are the same or different and each represent a hydrogen atom, a methyl group or a hydroxymethyl group, R represents a methyl group, a hydroxymethyl group or the following formula:

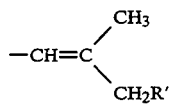

wherein R' represents a carboxyl group, a hydroxymethyl group or an acetoxymethyl group.

Deferriferrichromes of formula (I) are, for example, deferriferricrocin, deferriferrichrome, deferriferrichrome A, deferriferrichrome C, deferriferrichrysin, deferriferrirubin, deferriferrirhodin, deferriasperchrome $B_1$, deferriasperchrome $B_2$, deferriasperchrome $D_1$, deferriasperchrome $D_2$, deferriasperchrome $D_3$, deferriasperchrome C and deferriasperchrome A. These deferriferrichromes may be used singly or in the form of a mixture thereof.

Deferriferrichromes (I) used as an active ingredient in the present herbicide may be produced by any method known to the art, and are not particularly limited by their preparative process.

Deferriferrichromes (I) can be produced e.g. by treating ferrichromes of formula (II) with a base, an acid, or a substance capable of forming a complex compound.

Ferrichromes of formula (II) used herein as starting material can be obtained from a wide variety of microorganisms.

Out of the ferrichromes of formula (II), ferricrocin ($X_1 = CH_2OH$, $X_2 = H$, $R = CH_3$), for example, can be isolated from a culture medium of a microorganism (*C. gloeosporioides*) belonging to the genus Colletotrichum, as follows: The microorganism *C. gleoesporoides* is cultured for about 1 week on a solid culture (whose composition is set forth below) of Dr. Cutler et al., followed by extracting the culture with acetone. The extract is further extracted with ethyl acetate and then separated into an ethyl acetate-soluble fraction and a water-soluble fraction. Each fraction is applied to the cut face of cowpea blade for screening of a fraction having a weed-killing activity. The water-soluble fraction is purified through an HP-20 column (45% methanol) and then fractionated through a silica gel column (chloroform : methanol : aqueous system). Fractions having a weed-killing activity were combined and further fractionated by high performance liquid chromatography 3 times (reverse phase chromatography: twice, gel filtration chromatography: once), thus giving rise to purified ferricrocin.

Composition of the solid culture of Dr. Cutler et al.

| | |
|---|---|
| Shredded weed (available from Nabisco Co., Ltd. | 100 g |
| Mycological broth (DIFCO Co., Ltd. | 10 g |
| Yeast extract (DIFCO Co., Ltd. | 4 g |
| Sucrose | 40 g |
| Water | 200 ml |

Alternatively, the ferrichromes of formula (II) containing ferricrocin, ferrichrome, ferrichrome A and ferrichrome C, can be obtained in a large amount in a conventional method from a variety of mold fungi (see e.g. Eur. J. Appl. Microbiol. Biotechnol., 5(1), 51 (1978), Biochem., 5, 3694 (1966), Bio Metals, 4, 176 (1991), and FEBS Lett., 173(1), 53 (1984)).

Ferrichromes (II) obtained as described above can be converted into deferriferrichromes (I) by the Jalal method in which 8-hydroxyquinoline is added to a 50% methanol solution of ferrichromes (II) and then the mixture is allowed to react, followed by extraction with chloroform (see J. Org. Chem., 50, 5642 (1985).).

Deferriferrichromes (I) exhibit a strong weed-killing effect on broad-leaved weeds as well as on weeds belonging to the family Gramineae. Furthermore, the compounds have a nonselective weed-killing effect and work very quickly. The objective weeds include e.g. plants belonging to the family Leguminosae such as beggar weed, arrowroot(Pueraria lobata), etc.; the family Malvaceae such as velvet leaf, etc.; the family Rosaceae such as dandelion, etc.; and the family Gramineae such as barnyard grass, etc.

The herbicide of the present invention is produced usually by mixing deferriferrichromes (I) as an active ingredient with additives including a solvent, extender, carrier and regulatory agent. The herbicide thus prepared is used in the form of dust, granules, wettable powder, water-soluble powder, or the like.

The solid extender and carrier which can be used in the present herbicide include e.g. talc, clay, pumice, silica, synthetic calcium or magnesium silicate, diatomaceous earth, quartz, powdered cork, tripoli, grain flour, etc. The solvent used is e.g. water, methanol, acetone, dimethyl sulfoxide, or the like.

The surface active agent which can be used in the present herbicide includes e.g. octylphenyl polyoxyethanol, polyoxyethylene dodecyl ethers, polyoxyethylene sorbitan fatty esters, polyoxyethylene alkyl aryl ethers, etc.

Where the present herbicide is used as an water-soluble powder, the active ingredient used is usually in a concentration of 0.01–5.0%, preferably 0.07–1.0%.

The present herbicide can be used by applying it to the surface of a soil or by admixing it into a soil, in addition to spraying it directly onto weeds.

The present herbicide is applied usually in an amount of approx. 10–300 g/10a, preferably approx. 20–200 g/10a, in terms of active ingredient, depending on the type of objective weeds and objective agricultural products and application mode.

BEST MODE FOR CARRYING OUT THE INVENTION

The present invention is described in more detail by reference to the following examples, which however are not intended to limit the scope of the present invention.

Example 1

5 days after seeded, blades of velvet leaf (Indian mallow) were cut off from the roots, and the cut faces of blades were put in 0.75 ml each of aqueous solutions of the present herbicide deferriferricrocin ($X_1 = CH_2OH$, $X_2 = H$, $R = CH_3$) in glass tubes in concentrations of $10^{-2}$ M, $10^{-3}$ M, $10^{-4}$ M, $10^{-5}$ M and $10^{-6}$ M, respectively. Distilled water was used as a control group.

The criteria used for the evaluation of weed-killing activity are as follows:

+++: Complete withering of blades.
++: Withering of approximately half blades.
+: Withering of the peripheries of blades.
±: No observable effect.
−: The same as the control group.

As comparative examples, aqueous solutions of glyphosate and bialaphos were evaluated as conventional herbicides in the same manner for their weed-killing activity in concentrations of $10^{-2}$ M, $10^{-3}$ M, $10^{-4}$ M, $10^{-5}$ M and $10^{-6}$ M, respectively.

The results are set forth in Table 1.

TABLE 1

| concentration | the present invention deferriferricrocin | comparative examples | |
|---|---|---|---|
| | | glyphosate | bialaphos |
| *1 day after the treatment* | | | |
| $10^{-2}$M | +++ | + | + |
| $10^{-3}$M | ++ | ± | + |
| $10^{-4}$M | + | − | ± |
| $10^{-5}$M | − | − | − |
| $10^{-6}$M | − | − | − |
| *5 days after the treatment* | | | |
| $10^{-2}$M | +++ | +++ | + |
| $10^{-3}$M | ++ | ++ | + |
| $10^{-4}$M | + | − | + |
| $10^{-5}$M | − | − | − |
| $10^{-6}$M | − | − | − |

It is evident from Table 1 that, 1 day after the treatment, the present herbicide demonstrated a weed-killing activity superior to those of glyphosate and bialaphos. 5 days after the treatment, the present herbicide exhibited a weed-killing activity superior to that of bialaphos and almost equal to that of glyphosate. The present herbicide showed a satisfactory weed-killing effect in the concentrations of $10^{-2}$ and $10^{-3}$ M.

Example 2

2 weeks after seeded, intact cowpea blades were treated with 2 μl each of aqueous solutions of the present herbicide deferriferricrocin in concentrations of $10^{-2}$ M, $10^{-3}$ M, $10^{-4}$ M, $10^{-5}$ M and $10^{-6}$ M, respectively. Distilled water was used as a control group. 10 days later, changes in the peripheries of the treated parts were evaluated, and the results are set forth in Table 2.
The criteria used for the evaluation of weed-killing activity are as follows:
+++ Appearance of a withered part of 1.5 cm or more diameter.
++: Appearance of a withered part of 5 mm or more and less than 1.5 cm diameter.
+: Appearance of a withered part of less than 5 mm diameter.
±: No observable effect.
−: The same as the control group.

As comparative examples, aqueous solutions of the conventional herbicides glyphosate and bialaphos were evaluated in the same manner for their weed-killing activity in concentrations of $10^{-2}$ M, $10^{-3}$ M, $10^{-4}$ M, $10^{-5}$ M and $10^{-6}$ M, respectively.

The results are set forth in Table 2.

TABLE 2

| concentration | the present invention deferriferricrocin | comparative examples | |
|---|---|---|---|
| | | glyphosate | bialaphos |
| $10^{-2}$M | + | − | + |
| $10^{-3}$M | + | − | + |
| $10^{-4}$M | ± | − | + |
| $10^{-5}$M | − | − | − |
| $10^{-6}$M | − | − | − |

As is evident from Table 2, the present herbicide exhibited a weed-killing activity superior to that of glyphosate and almost equal to that of bialaphos.

Example 3

Velvet leaf, barnyard grass, radish, beggar weed and foxtail were seeded respectively in 2 pots (10 cm×10 cm) and were then grown for 10 days in a greenhouse. The plant in each pot was sprayed with 2 ml of an aqueous solution of the present herbicide ($10^{-2}$ and $10^{-3}$ M deferriferricrocin), and the plants were evaluated 7 days later. Distilled water was used as a control group.

The criteria used for the evaluation of weed-killing activity are as follows:
+++: Withering.
++: Significantly poor growth.
+: Poor growth.
±: Somewhat (but unobservable) poor growth.
−: Strong growth (the same as the control group).

As a comparative example, aqueous solutions of the conventional herbicide bialaphos were evaluated in the same manner for their weed-killing activity concentrations of $10^{-2}$ M and $10^{-3}$ M, respectively.

The results are set forth in Table 3.

TABLE 3

| object weeds | the present invention deferriferricrocin | | comparative example bialaphos | |
|---|---|---|---|---|
| | $10^{-2}$M | $10^{-3}$M | $10^{-2}$M | $10^{-3}$M |
| velvet leaf | ++ | ± | ++ | ± |
| barnyard gras | + | ± | ++ | ± |
| radish | + | ± | ++ | ± |
| beggar weed | ++ | + | ++ | ± |
| foxtail | + | ± | ++ | ± |

As is evident from Table 3, the present herbicide exhibited a weed-killing activity almost comparable to that of bialaphos.

Example 4

In the same manner as in Example 1 where aqueous solutions of deferriferricrocin were used, blades of velvet leaf 5 days after seeded were cut off from the roots, and the cut faces of blades were put in 0.75 ml each of aqueous solutions of the present herbicides (3 kinds of deferriferrichromes) in glass tubes in concentrations of $10^{-2}$ M, $10^{-3}$ M, $10^{-4}$ M, $10^{-5}$ M and $10^{-6}$ M, respectively.

The criteria used for the evaluation of weed-killing activity were the same as in Example 1.

As comparative examples, aqueous solutions of the conventional herbicides glyphosate and bialaphos were evaluated in the same manner for their weed-killing activity in concentrations of $10^{-2}$ M, $10^{-3}$ M, $10^{-4}$ M, $10^{-5}$ M and $10^{-6}$ M, respectively.

The results are set forth in Table 4.

TABLE 4

| concentration | the present invention | | | comparative examples | |
|---|---|---|---|---|---|
| | deferriferrichrome A | deferriferrichrome | deferriferrichrome C | glyphosate | bialaphos |
| *1 day after the treatment* | | | | | |
| $10^{-2}$M | + | ++ | ++ | + | + |
| $10^{-3}$M | + | + | + | ± | + |
| $10^{-4}$M | ± | ± | ± | − | ± |
| $10^{-5}$M | − | − | − | − | − |
| $10^{-6}$M | − | − | − | − | − |
| *5 days after the treatment* | | | | | |
| $10^{-2}$M | + | ++ | ++ | ++ | ++ |
| $10^{-3}$M | + | + | + | + | + |
| $10^{-4}$M | ± | ± | ± | − | + |
| $10^{-5}$M | − | − | − | − | − |

TABLE 4-continued

| | the present invention | | | comparative examples | |
|---|---|---|---|---|---|
| concentration | deferri-ferrichrome A | deferri-ferrichrome | deferri-ferrichrome C | glyphosate | bialaphos |
| $10^{-6}$M | − | − | − | − | − | deferriferrichrome: $X_1 = H$, $X_2 = H$, $R = CH_3$
deferriferrichrome C: $X_1 = CH_3$, $X_2 = H$, $R = CH_3$
deferriferrichrome A: $X_1 = X_2 = CH_2OH$, $$R = \underset{H}{\overset{}{\diagdown}} C = C \underset{CH_2COOH}{\overset{CH_3}{\diagup}}$$

As is evident from Table 4, the weed-killing activity of 3 deferriferrichromes is comparable to that of deferriferricrocin shown in Example 1.

Example 5

In the same manner as in Example 2 where aqueous solutions of deferriferricrocin were used, intact cowpea blades 2 weeks after seeded were treated with 2 μl each of aqueous solutions of the present herbicide composed of 2 deferriferrichromes (i.e., deferriferrichrome and deferriferrichrome C) in concentrations of $10^{-2}$ M, $10^{-3}$ M, $10^{-4}$ M, $10^{-5}$ M and $10^{-6}$ M, respectively. 10 days later, changes in the peripheries of the treated parts were evaluated, and the results are shown in Table 5.

The criteria used for the evaluation of weed-killing activity are the same as in Example 2.

As comparative examples, aqueous solutions of the conventional herbicides glyphosate and bialaphos were evaluated in the same manner for their weed-killing activity in concentrations of $10^{-2}$ M, $10^{-3}$ M, $10^{-4}$ M, $10^{-5}$ M and $10^{-6}$ M, respectively.

The results are set forth in Table 5.

TABLE 5

| | the present invention | | comparative examples | |
|---|---|---|---|---|
| concentration | deferri-ferrichrome | deferriferri-chrome C | glyphosate | bialaphos |
| $10^{-2}$M | + | + | − | + |
| $10^{-3}$M | + | + | − | + |
| $10^{-4}$M | ± | ± | − | + |
| $10^{-5}$M | − | − | − | − |
| $10^{-6}$M | − | − | − | − |

As is evident from Table 5, 2 kinds of deferriferrichromes exhibited a weed-killing activity comparable to that of deferriferricrocin shown in Example 2.

Example 6

Velvet leaf, barnyard grass, radish, beggar weed and foxtail were seeded respectively in 2 pots (10 cm × 10 cm) and were then grown for 15 days in a greenhouse. The plant in each pot was sprayed with 2 ml each of aqueous solutions of the present herbicide deferriferrichrome in concentrations of $10^{-2}$ and $10^{-3}$ M, respectively, and the plants were evaluated 7 days later.

The criteria used for the evaluation of weed-killing activity are the same as in Example 3.

As comparative examples, aqueous solutions of the conventional herbicide bialaphos were evaluated in the same manner for their weed-killing activity in concentrations of $10^{-2}$ and $10^{-3}$ M, respectively.

The results are set forth in Table 6.

TABLE 6

| | the present invention deferriferrichrome | | comparative example bialaphos | |
|---|---|---|---|---|
| object weeds | $10^{-2}$M | $10^{-3}$M | $10^{-2}$M | $10^{-3}$M |
| velvet leaf | + | ± | ++ | + |
| barnyard grass | + | ± | + | − |
| radish | + | ± | ++ | + |
| beggar weed | + | + | + | + |
| foxtail | + | ± | + | ± |

It is evident from Table 6 that, as is the case with deferriferricrocin shown in Example 3, deferriferrichrome exhibited a weed-killing activity comparable to that of the comparative example bialaphos.

Example 7 Wettable powder

A mixture of 20% deferriferrichromes (I), 75% kaolin and 5% sodium higher alkyl sulfate was homogeneously ground and mixed to give wettable powder.

Example 8 Dust

A mixture of 1% deferriferrichromes (I), 97% of a 1 : 1 mixture of talc and calcium carbonate and 2% silicic acid anhydride was homogeneously ground and mixed to give dust.

Example 9 Granule

A mixture of 2% deferriferrichromes (I), 48% fine bentonite powder, 48% talc and 2% sodium lignin sulfonate was homogeneously ground and mixed, followed by addition of water. The mixture was kneaded, then granulated, and dried to give granules.

INDUSTRIAL APPLICABILITY

The herbicide of the present invention exhibits a strong weed-killing effect on a wide range of plants such as broad-leaved weeds as well as weeds belonging to the family Gramineae.

What is claimed is:

1. A method for controlling the growth of weeds which comprises applying a herbicidally effective amount of a composition comprising as an active ingredient a compound represented by the following formula (I) directly onto weeds, onto the surface of soil or into soil in which weeds may grow:

[Chemical structure of formula (I)]

wherein $X_1$ and $X_2$ are the same or different and each represent a hydrogen atom, a methyl group or a hydroxymethyl group, R represents a methyl group, a hydroxymethyl group or the following formula:

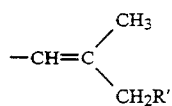

wherein R' represents a carboxyl group, a hydroxymethyl group or an acetoxymethyl group.

2. The method according to claim 1, wherein the active ingredient is selected from the group consisting of deferriferricrocin, deferriferrichrome, deferriferrichrome A, deferriferrichrome C, deferriferrichrysin, deferriferrirubin, deferriferrirhodin, deferriasperchrome B$_1$, deferriasperchrome B$_2$, deferriasperchrome D$_1$, deferriasperchrome D$_2$, deferriasperchrome D$_3$, deferriasperchrome C, deferriasperchrome A and mixtures thereof.

3. The method according to claim 1 wherein the active ingredient is at least one compound selected from the group consisting of deferriferricrocin, deferriferrichrome, deferriferrichrome A and deferriferrichrome C.

4. The method according to claim 3, wherein the herbicidal composition is applied in an amount of 20–200g/10a in terms of the active ingredient.

5. The method according to claim 4, wherein the active ingredient is deferriferricrocin.

6. The method according to claim 4, wherein the active ingredient is deferriferrichrome.

7. The method according to claim 4, wherein the active ingredient is deferriferrichrome C.

8. The method according to claim 1, wherein the active ingredient is deferriferricrocin.

9. The method according to claim 1, wherein the active ingredient is deferriferrichrome.

10. The method according to claim 1, wherein the active ingredient is deferriferrichrome C.

11. The method according to claim 1, wherein the weeds are selected from the group consisting of Leguminosae, Malvaceae, Rosaceae and Gramineae.

12. The method according to claim 1, wherein said composition is in the form of dust, granules, wettable powder, or water-soluble powder.

13. The method according to claim 1, wherein said active ingredient is present in a concentration of 0.01–5.0%.

14. The method according to claim 1, wherein the herbicidal composition is applied in an amount of 10–300g/10a in terms of the active ingredient.

15. The method according to claim 1, wherein the herbicidal composition is applied in an amount of 20–200g/10a in terms of the active ingredient.

* * * * *